United States Patent [19]

Pontoglio et al.

[11] Patent Number: 4,808,345

[45] Date of Patent: Feb. 28, 1989

[54] PROCESS FOR THE PREPARATION OF TETRACHLOROTEREPHTHALOYL DICHLORIDE BY MEANS OF THE CHLORINATION OF TEREPHTHALOYL DICHLORIDE WITH GASEOUS CHLORINE

[75] Inventors: Enrico Pontoglio, Brescia; Sandro Parodi, Nuvolento; Giuseppe Ghielmetti, Milan; Liborio Casale, Brescia, all of Italy

[73] Assignee: CAFFARO S.p.A. Societa per l'Industria Chimica ed Elettrochimica, Milan, Italy

[21] Appl. No.: 856,335

[22] Filed: Apr. 28, 1986

[51] Int. Cl.$^4$ .............................................. C07C 63/30
[52] U.S. Cl. ............................ 260/544 D; 260/544 P; 260/694
[58] Field of Search .......... 260/544 D, 544 M, 544 P, 260/694

[56] References Cited

U.S. PATENT DOCUMENTS 3,108,130 10/1963 Haga et al. ............................ 260/694

3,833,652 9/1974 Knobloch ........................ 260/544 D

OTHER PUBLICATIONS

Kalbach, John C., *Chemical Engineering*, Jan. 1947, pp. 105–108.

Rabjohn, Norman, *J. Am. Chemical Society*, vol. 70 (1948), p. 3518.

*Primary Examiner*—Paul J. Killos
*Attorney, Agent, or Firm*—Stevens, Davis, Miller & Mosher

[57] ABSTRACT

The invention relates to a process for the preparation of tetrachloroterephthaloyl dichloride by means of the chlorination of terephthaloyl dichloride with gaseous chlorine, characterized in that said chlorination is carried out in the vapor phase in the presence of activated charcoal as catalyst. The invention relates also to the synthesis processes in which the compound prepared according to the process said is used as an intermediate.

8 Claims, No Drawings

PROCESS FOR THE PREPARATION OF TETRACHLOROTEREPHTHALOYL DICHLORIDE BY MEANS OF THE CHLORINATION OF TEREPHTHALOYL DICHLORIDE WITH GASEOUS CHLORINE

It is well known that the tetrachloroterephthaloyldichloride has become an industrially interesting compound since when it became a valuable intermediate in the production of methyl 2,3,5,6-tetrachloroterephthalate; this latter is a compound which was prepared for the first time in 1948 by chlorination of terephthaloyl dichloride and subsequent reaction with methanol (Rabjohn, N., J. Am Chem. Soc., 1948, 70, 3518), and proposed for use as pre-emergence herbicide in 1960 (U.S. Pat. No. 2,923,634).

The critical step in the preparation of dimethyl tetrachloroterephthalate is precisely the chlorination of terephthaloyl dichloride, which is carried out batchwise, requires high temperatures, rather high clorine pressures and quite long reaction times; the consequence of such severe conditions of reaction is the formation of undesirable byproducts, such as hexachlorobenzene, which are noxious both because of their toxicity, and because they reduce the reaction yield. Moreover, the resulting product is contaminated by the residues of the catalyst. Further, the product cannot be used in the development of agrochemicals without more due to the presence of more than 500 ppm of hexachlorobenzene.

In U.S. Pat. No. 3,052,712, a process is disclosed for the production of tetrachloroterephthaloyl dichloride, in which this product is obtained by the chlorination of raw terephthaloyl dichloride, as it comes out from the reaction of synthesis, preferably at temperatures of from 170° to 190° C., and under pressures of from 6 to 8 atmospheres, with reaction times of from 8 to 12 hours, in the presence of ferric chloride as the catalyst, in a quantity of about 1%.

The tetrachloroterephthaloyl dichloride which is thus obtained rarely has a purity level higher than 90%, due to the presence of noticeable quantities of byproducts, among which is hexachlorobenzene, a compound well known for its toxicity, and one which tends to accumulate in the environment and in the animal tissues. The tetrachloroterephthaloyl dichloride contains additionally undesirable residues of the halogenation catalyst, which confer a brownish color to the product obtained from the subsequent esterification reaction.

In the Belgian Pat. No. 629,377, for the purpose of trying to eliminate the drawback of the dark color formation in the ester, resort is had to the addition of substances capable of forming slightly colored or water-soluble complexes with the catalyst, while according to U.S. Pat. No. 3,402,195, resort is had to the recrystallization of said catalyst with xylene.

A purpose of the present invention is to provide a chlorination process of terephthaloyl dichloride which, in comparison to the previously mentioned process, is more advantageous as for selectivity and yield, and which can be carried out continuously.

In particular, the tetrachloroterephthaloyl dichloride whose obtainment is desired within the purposes of the present invention, must be of high purity level, with a content not less than 95% of the main compound and not more than 500 ppm of hexachlorobenzene by-product, so that the high purity and the total absence of catalyst residues allow a high purity end product to be obtained from the esterification with methanol, the color of such end product moreover being such, as not to require expensive purification operations.

A further purpose of the instant invention is to develop a process which allows tetrachloroterephthaloyl dichloride to be directly obtained in a powder form, which is a convenient physical form for its subsequent use.

These purposes are achieved by the chlorination of terephthaloyl dichloride with gaseous chlorine, characterized in that said chlorination is carried out in the vapor phase, in the presence of activated charcoal as the catalyst.

According to a preferred embodiment, the process of the instant invention is carried out by introducing into a reaction vessel vapors of terephthaloyl dichloride, gaseous chlorine and an inert gas, in a fluidized bed of particles of activated charcoal. During the reaction, the fluidized bed is maintained at the desired temperature, of at most 250° C., by withdrawing the excess of reaction heat by means of suitable cooling systems (e.g., tubes inside the reactor). The mixture of reaction gases outcoming from the reactor is cooled in a desublimator in which tetrachloroterephthaloyl dichloride is recovered as a solid, generally as a white microcrystalline powder, which is recovered continuously. Downstream of the fluid bed reactor, in which the greatest part of the heat is disposed of, upstream of the desublimator a second reactor may be installed, with a fixed bed of activated charcoal, which acts as a finishing reactor, so as to complete the reaction, making the main reactor operate under the least severe conditions as possible, so as to minimize the formation of undesirable byproducts, and to increase the life of the catalyst.

The operative conditions adopted may vary within quite broad limits, in function of the several reaction parameters. The temperature of catalytic beds may be comprised between 200° and 250° C., preferably between 230° and 240° C.

In general, an excessive lowering of the temperature makes it difficult to withdraw the chlorinated product from the catalytic bed, and consequently its recovery, while too high temperatures cause the detaching of carbonyl groups by chlorolysis, thus leading to undesirable byproducts.

The exothermicity of the chlorination reaction generates large quantities of heat, which can cause local overheatings inside the catalytic layer. For the purpose of preventing such occurrence, inert dilutants can be used, feeding into the feeding stream of the reactor, consisting of chlorine and terephthaloyl dichloride, inert gases such as nitrogen, hydrochloric acid, $CCl_4$.

The inert dilutant facilitates also the recovery of the product by desublimation. Generally, the quantity of inert gases is that which is sufficient for the purpose of maintaining the bed of activated charcoal in a fluidized state. However, the % by volume of the dilutant inside the feeding stream of the reactants may be varied quite broadly within the range of from 10% to 90%, preferably of from 50 to 85%.

These dilutants, as well as the excess chlorine possibly remaining may be totally or partly recycled after having purged away the hydrochloric acid formed during the reaction.

The molar ratio of chlorine to terephthaloyl dichloride may be within the range of from 4 to 10, but an excess of chlorine is preferably used of from 1.2 to 1.6 times the stoichiometric quantities. A too large excess of chlorine, even when the temperature is low, and the reaction is carried out in the presence of a large quantity of dilutants, facilitates breakdown and overchlorination reactions.

Also the contact time of the substances reacting within the catalytic beds may be selected inside a broad range of values. Such time shall practically depend on the catalytic activity of the charcoal used, on the reaction temperature, and on other parameters, well known to those skilled in the art.

In general, under the experimental conditions, a time was used between 2 and 20 seconds, preferably between 3 and 10.

The reaction is usually carried out under the atmospheric pressure, but it is possible as well to carry out the synthesis under a slight over-pressure.

In the process claimed it is also mandatory that the catalyst used by activated charcoal. It shall be in a microgranular form suitable to the conditions of fluidification, with a granulometry preferably comprised between 0.1 and 0.4 mm.

For the purpose of illustrating the process in more detail, the following Examples are reported, which shall not be constructed as being in any way limitative of the invention.

EXAMPLE I

A gaseous mixture consisting of chlorine (0.375 mole/hour), nitrogen (2.557 mole/hour) and technical grade terephthaloyl dichloride, vaporized (0.065 mole/hour) is fed to the bottom of a glass tubular reactor, having a diameter of 4 cm and a length of 20 cm, equipped in its lower part with a porous diaphragm, externally heated along its whole length by electrical resistors, and previously charged with 64 g of activated charcoal in granular form (0.1–0.2 mm).

The flow rate of the feeding stream is such as to secure the fluidification of the catalytic bed, and a contact time of about 5 seconds.

The reaction is carried out continuously for eight hours at the temperature of 230° C. The gases and the vapors escaping from the top of the reactor are cooled inside a collecting vessel at room temperature. Inside such a vessel, the chlorinated product desublimates as a crystalline powder, of white color and of fine consistency, while the gases ($N_2$, HCl and $Cl_2$) are sent to a laying system, consisting of a small tower where sodium hydroxide circulates.

The conversion is practically total and the gas-chromatographic analysis shows that the product is 2,3,5,6-tetrachloroterephthaloyl dichloride at a purity of 97.5%. The amount of hexachlorobenzene is 350 ppm.

EXAMPLE II

To the basis of the same reactor described in Example I, and by operating in the same way, vaporized terephthaloyl dichloride (0.132 mole/hour), chlorine (0.738 mole/hour) and nitrogen (2.357 mole/hour) are continuously fed for about 5 hours at the reaction temperature of 240° C.

The gas-chromatography of the chlorinated solid product collected in the desublimator shows that it is tetrachloroterephthaloyl dichloride with a purity of 96.1%. The amount of hexachlorobenzene is approximately 470 ppm. Such a value is totally satisfactory if it is borne in mind that it is obtained directly in the synthesis without purification and with a purity greater than 95%.

EXAMPLE III

To the basis of the reactor, described in preceding Examples, the mixture of vaporized terephthaloyl dichloride (0.080 mole/hour), chlorine (0.530 mole/hour) and nitrogen (2.557 mole/hour) is continuously fed for 7 hours and 30 minutes, at the maximum reaction temperature of 225° C. The vapors and the gases outcoming from the top of reactor are introduced, while being still hot, in a second tubular reactor, of about 6 cm of height, charged with activated charcoal of suitable granulometry, so that the catalytic bed remains fixed, and maintained at the temperature of 235° C. The product collected by desublimation following the method as previously described, and submitted to the gas-chromatographic analysis, shows a content of tetrachloroterephthaloyl dichloride of 98.1%. The amount of hexachlorobenzene is approximately 415 ppm.

From what has been described hereinabove, it can be therefore understood that in general the invention allows the initially discussed purposes to be efficaciously achieved: a product is indeed obtained with high purity level, with a very low content of toxic byproducts and without residues from the catalyst, additionally as a microcrystalline white powder which does not require any purification treatments before being sent to the following synthetic processes. Moreover, the reaction conditions according to the invention are certainly more favorable than those required by the known process, mainly because it is not required to operate under high pressure, nor for long times. On the contrary, the reaction times of the invention can also be very short, with evident financial and operating advantages.

Moreover, to a discontinuous chlorination process, the instant invention opposes a continuous synthesis, in which the tetrachloroterephthaloyl dichloride produced can be separated continuously in an absolutely convenient way, by means of a simple cooling step inside a desublimator, and at a practically pure state.

The whole of these advantages presented by the invention allows an unquestionable technical progress in this field.

We claim:

1. In a process for the chlorination of terephthaloyl dichloride to produce tetrachloroterephthaloyl dichloride, wherein the improvement comprises chlorinating terephthaloyl dichloride in the vapor phase with gaseous chlorine in the presence of activated charcoal as a catalyst in microgranular form suitable for fluidization, at a temperature in the range of between 230° to 240° C. so that less than 500 ppm of hexachlorobenzene by-product is produced.

2. Process as claimed in claim 1, characterized in that the process is carried out as a continuous process.

3. Process as claimed in claim 1, characterized in that said activated charcoal is maintained in a fluidized bed.

4. Process as claimed in claim 1, characterized in that said activated charcoal is maintained in a fluidized bed and in a separate fixed bed.

5. Process as claimed in claim 1, characterized in that in the process a gaseous mixture is used of chlorine and one or more dilutant(s) selected from the group consisting of nitrogen, hydrochloric acid and carbon tetrachloride.

6. Process as claimed in claim 1, characterized in that said chlorination is carried out at a temperature selected within the range of from 230°–240° C., with a reaction time selected within the range of from 2 to 20 seconds.

7. Process as claimed in claim 1, characterized in that the tetrachloroterephthaloyl dichloride produced is separated from the gaseous reaction mixture by means of desublimation by cooling.

8. Process as claimed in claim 1, characterized in that said chlorination is carried out in a first stage in which said activated charcoal is maintained in a fluid bed, and in a second stage of completion of the reaction in which said activated charcoal is maintained in a fixed bed.

* * * * *